(12) United States Patent
Wilschke et al.

(10) Patent No.: US 10,973,531 B2
(45) Date of Patent: Apr. 13, 2021

(54) KERRISON RONGEUR WITH REMOVABLE TIP ASSEMBLY

(71) Applicant: CareFusion 2200, Inc., San Diego, CA (US)

(72) Inventors: Thomas Wilschke, Chicago, IL (US); Michael Plishka, Lake Villa, IL (US)

(73) Assignee: CareFusion 2200, Inc., San Diego, CA (US)

( * ) Notice: Subject to any disclaimer, the term of this patent is extended or adjusted under 35 U.S.C. 154(b) by 22 days.

(21) Appl. No.: 15/636,124

(22) Filed: Jun. 28, 2017

(65) Prior Publication Data
US 2019/0000488 A1      Jan. 3, 2019

(51) Int. Cl.
*A61B 17/16*     (2006.01)
*A61B 90/00*     (2016.01)
*A61B 17/00*     (2006.01)

(52) U.S. Cl.
CPC ...... *A61B 17/1604* (2013.01); *A61B 17/1611* (2013.01); *A61B 2017/00367* (2013.01); *A61B 2017/00473* (2013.01); *A61B 2017/00477* (2013.01); *A61B 2017/00526* (2013.01); *A61B 2090/0813* (2016.02)

(58) Field of Classification Search
CPC ............ A61B 17/1608; A61B 17/1611; A61B 17/1606; A61B 17/1604
See application file for complete search history.

(56) References Cited

U.S. PATENT DOCUMENTS

| 6,142,997 A | 11/2000 | Michelson |
| 7,297,147 B2 | 11/2007 | Michelson |
| 8,657,823 B2 | 2/2014 | Agbodoe |
| 2002/0151931 A1* | 10/2002 | Tontarra ............ A61B 17/1611 606/205 |
| 2004/0044346 A1 | 3/2004 | Boury |
| 2013/0150861 A1* | 6/2013 | Agbodoe ........... A61B 17/1608 606/83 |
| 2018/0000514 A1* | 1/2018 | Koller ................ A61B 17/1611 |

FOREIGN PATENT DOCUMENTS

| DE | 202005019304 U1 | 2/2006 |
| DE | 10 2008 034 287 B4 | 2/2010 |
| DE | 202016103158 U1 | 6/2016 |
| WO | 2009141320 A1 | 11/2009 |

OTHER PUBLICATIONS

International Preliminary Report on Patentability dated Dec. 31, 2019 pertaining to International Application No. PCT/US2018/039526.

* cited by examiner

*Primary Examiner* — Amy R Sipp
(74) *Attorney, Agent, or Firm* — Dinsmore & Shohl LLP

(57) ABSTRACT

A rongeur includes a device body having a first arm and a second arm slidably coupled to the first arm. A handle operatively coupled to the first arm and the second arm is configured to move the second arm along a length of the first arm in a first direction and an opposing second direction. A tip assembly is removably coupled to a distal end of the device body. The tip assembly includes a first tip and a second tip slidably coupled to the first tip. A locking mechanism is configured to removably couple the first tip to the first arm and removably couple the second tip to the second arm. The second tip is movable with respect to the first tip from an open position toward a closed position as the second arm moves in the first direction.

11 Claims, 8 Drawing Sheets

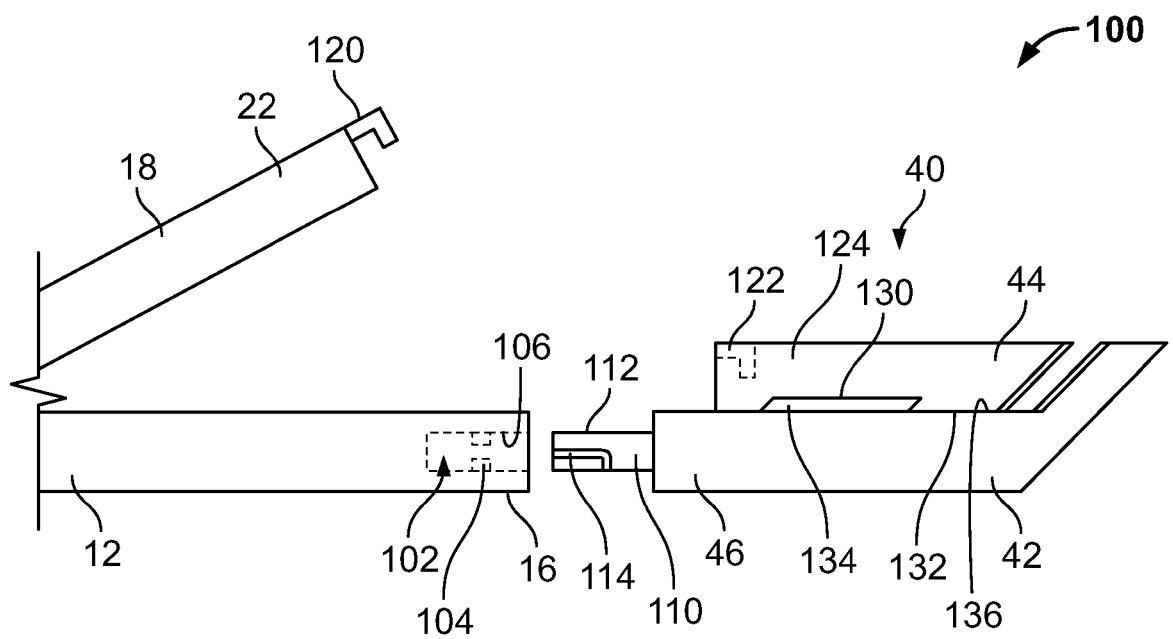
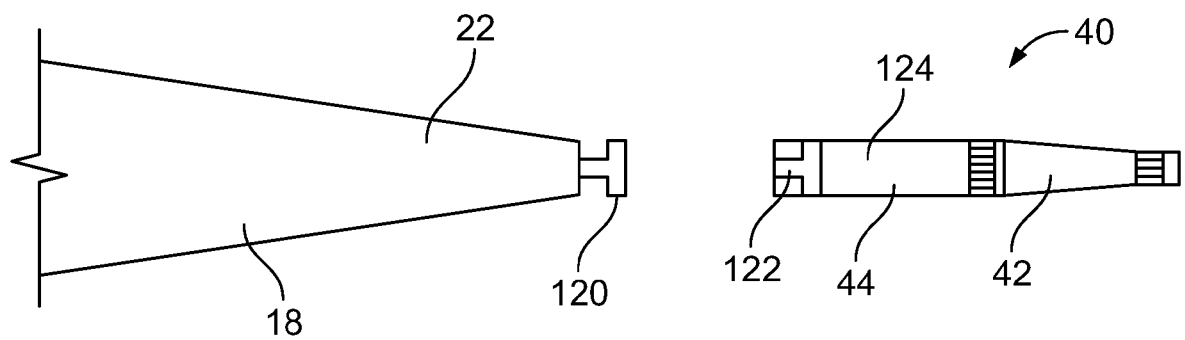

KERRISON RONGEUR WITH REMOVABLE TIP ASSEMBLY

CROSS-REFERENCE TO RELATED APPLICATIONS

N/A

TECHNICAL FIELD

The present application relates generally to a medical device including one or more replaceable cutting tips. More specifically, the present application relates to a rongeur, such as a Kerrison rongeur, having a tip assembly removably coupled at a distal end of the rongeur that includes replaceable and disposable cutting tips.

BACKGROUND

Rongeurs, such as Kerrison rongeurs, must have sharp cutting tips to accurately perform delicate surgery around the skull and the spinal column of a patient. The cutting tips quickly become dull, requiring sharpening after a limited number of cutting procedures through hard bone and strong tendons and ligaments. Many conventional cutting tips may only be used in 10-15 procedures before such sharpening is required. Further, due to the relatively small dimensions of the cutting tips, many cutting tips can only be sharpened 8-10 times before they are no longer effective.

BRIEF SUMMARY OF SOME EXAMPLE EMBODIMENTS

In one aspect, a Kerrison rongeur includes a stationary arm. The stationary arm has a proximal end and an opposing distal end. A movable arm is slidably coupled to the stationary arm. The movable arm has a proximal end and an opposing distal end. A handle is operatively coupled to the stationary arm and the movable arm. In certain embodiments, a tip assembly is removably coupled in an assembled configuration to the distal end of the stationary arm and the distal end of the movable arm. The tip assembly includes a first tip and a second tip slidably coupled to the first tip. The second tip is slidably movable with respect to the first tip between an open position and a closed position. A locking mechanism is configured to removably couple the first tip to the stationary arm and removably couple the second tip to the movable arm. The second tip is slidably movable with respect to the first tip between the open position and the closed position as the movable arm is slidably movable with respect to the stationary arm.

In another aspect, a rongeur includes a device body. The device body includes a first arm having a proximal end and an opposing distal end. A second arm is slidably coupled to the first arm. The second arm has a proximal end and an opposing distal end. A handle is operatively coupled to the first arm and the second arm. The handle is configured to move the second arm along a length of the first arm in a first direction and an opposing second direction. A tip assembly is removably coupled to a distal end of the device body. The tip assembly includes a first tip and a second tip slidably coupled to the first tip. The second tip is movable with respect to the first tip between an open position and a closed position. A locking mechanism is configured to removably couple the first tip to the first arm and removably couple the second tip to the second arm. The second tip is movable with respect to the first tip from the open position toward the closed position as the second arm moves in the first direction.

In yet another aspect, a method for coupling a tip assembly to a Kerrison rongeur includes assembling a tip assembly. The tip assembly includes a first tip and a second tip slidably coupled to the first tip. In certain embodiments, the tip assembly is removably coupled in an assembled configuration to a distal end of a device body of the Kerrison rongeur.

BRIEF DESCRIPTION OF THE DRAWINGS

FIG. 3 is a partial side view of an example Kerrison rongeur having a removable tip assembly according to example embodiments;

FIG. 4 is a top view of the example Kerrison rongeur of FIG. 3;

DETAILED DESCRIPTION

Figure 1:
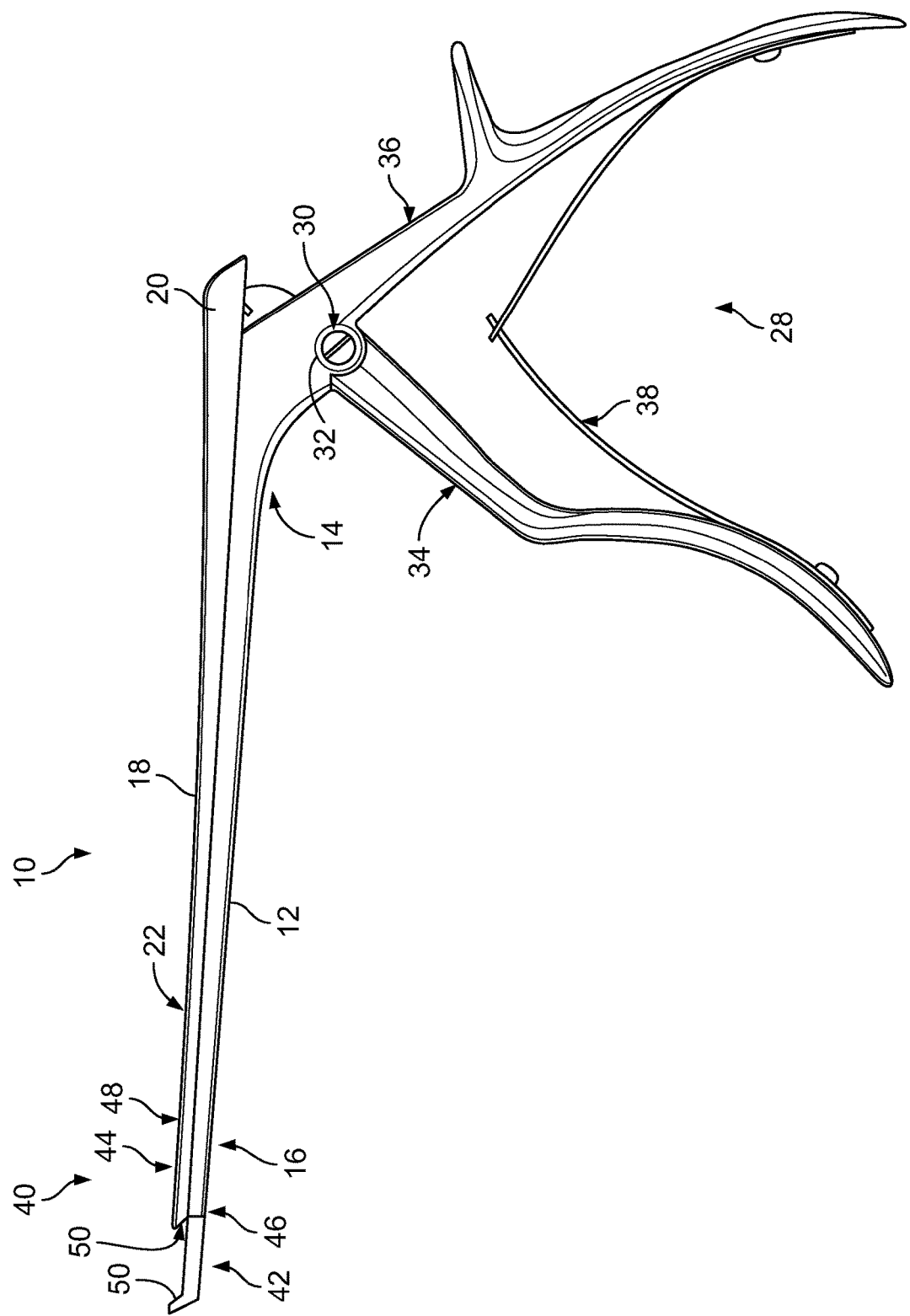
FIG. 1 is a side view of an example Kerrison rongeur having a removable tip assembly according to example embodiments.

Various embodiments are described below with reference to the drawings in which like elements generally are referred to by like numerals. The relationship and functioning of the various elements of the embodiments may better be understood by reference to the following detailed description. However, embodiments are not limited to those illustrated in the drawings. It should be understood that the drawings are not necessarily to scale, and in certain instances details may have been omitted that are not necessary for an understanding of embodiments disclosed herein, such as—for example—conventional fabrication and assembly.

The invention is defined by the claims, may be embodied in many different forms, and should not be construed as limited to the embodiments set forth herein; rather, these embodiments are provided so that this disclosure will be thorough and complete, and will fully convey enabling disclosure to those skilled in the art. As used in this specification and the claims, the singular forms "a," "an," and "the" include plural referents unless the context clearly dictates otherwise. Reference herein to any industry standards (e.g., ASTM, ANSI, IEEE standards) is defined as complying with the currently published standards as of the original filing date of this disclosure concerning the units, measurements, and testing criteria communicated by those standards unless expressly otherwise defined herein. The terms "proximal" and "distal" are used herein in the common usage sense where they refer respectively to a handle/doctor-end of a device or related object and a tool/patient-end of a device or related object. The terms "about," "substantially," "generally," and other terms of degree, when used with reference to any volume, dimension, proportion, or other quantitative or qualitative value, are intended to communicate a definite and identifiable value within the standard parameters that would be understood by one of skill in the art (equivalent to a medical device engineer with experience in this field), and should be interpreted to include at least any legal equivalents, minor but functionally-insignificant variants, standard manufacturing tolerances, and including at least mathematically significant figures (although not required to be as broad as the largest range thereof).

In example embodiments, a Kerrison rongeur includes a removable and replaceable tip assembly having two cutting tips, i.e., a first or bottom cutting tip and a second or top cutting tip; thus, providing the surgeon with the ability to select a sterile tip assembly having sharp cutting tips of a desired size for any scheduled procedure. The Kerrison rongeur includes a locking mechanism that removably couples and secures the tip assembly to a distal end of the device body. The locking mechanism is intended to be functional without changing the historical Kerrison rongeur handle size and/or geometry or the existing cutting tip sizes.

Unlike conventional devices, the example tip assemblies described herein allow the surgeon or an assistant to quickly and easily couple and release or remove the tip assembly from the device body, for example, using one hand to hold the device and the other hand to engage or disengage the locking mechanism. Additionally, certain embodiments described herein can be used in conjunction with a "take-apart" style Kerrison rongeur to provide an added benefit of easier and more effective cleaning and sterilization of the device body.

In example embodiments, the Kerrison rongeur includes a device body having a first or stationary arm. The first arm has a proximal end and an opposing distal end. A second or movable arm is slidably coupled to the first arm and configured to translate along a length of the first arm in a first direction, e.g., a distal direction, and a second direction opposite the first direction, e.g., a proximal direction. The second arm has a proximal end and an opposing distal end. A handle is operatively coupled to the first arm and the second arm. A tip assembly is removably coupled to a distal end of the device body. In certain embodiments, the tip assembly is removably coupled in an assembled configuration to the distal end of the first arm and/or the distal end of the second arm. In the assembled configuration, the tip assembly includes a first tip and a second tip slidably coupled to the first tip and configured to translate along a length of the first tip between a first, e.g., open, position and a second, e.g., closed, position. In certain embodiments, the first tip is removably coupled to the first arm and the second tip is removably coupled to the second arm. The second tip is slidably movable with respect to the first tip in cooperation with or as the second arm is slidably movable with respect to the first arm. The first tip and/or the second tip includes a cutting edge to cut biological material, such as bone or tissue, for example, as the second tip, coupled to the second arm, moves along a length of the first tip between the first position and the second position. A locking mechanism is configured to removably couple the tip assembly to the distal end of the device body. For example, the locking mechanism is configured to removably couple the first tip to the first arm and removably couple the second tip to the second arm.

In certain embodiments, the locking mechanism includes a first attachment member, e.g., a connector or fastener such as a pin, projection, peg, screw, rod, shaft, dowel, cylinder or bolt, for example, disposed at or near the proximal end of the first tip and a first receiving section, e.g., a void, opening, hole, groove, depression, slot, slit, aperture, cavity, orifice, space or recess, for example, disposed at or near the distal end of the first arm. The first receiving section is configured to receive and/or cooperate with the first attachment member. The locking mechanism also includes a second attachment member disposed at or near the proximal end of the second tip and a second receiving section disposed at or near the distal end of the second arm. The second receiving section is configured to receive the second attachment member. In certain alternative embodiments, the locking mechanism includes a first receiving section disposed at or near the proximal end of the first tip and a first attachment member disposed at or near the distal end of the first arm. The first receiving section is configured to receive the first attachment member. The locking mechanism also includes a second receiving section disposed at or near the proximal end of the second tip and a second attachment member disposed at or near the distal end of the second arm.

Figure 2A:
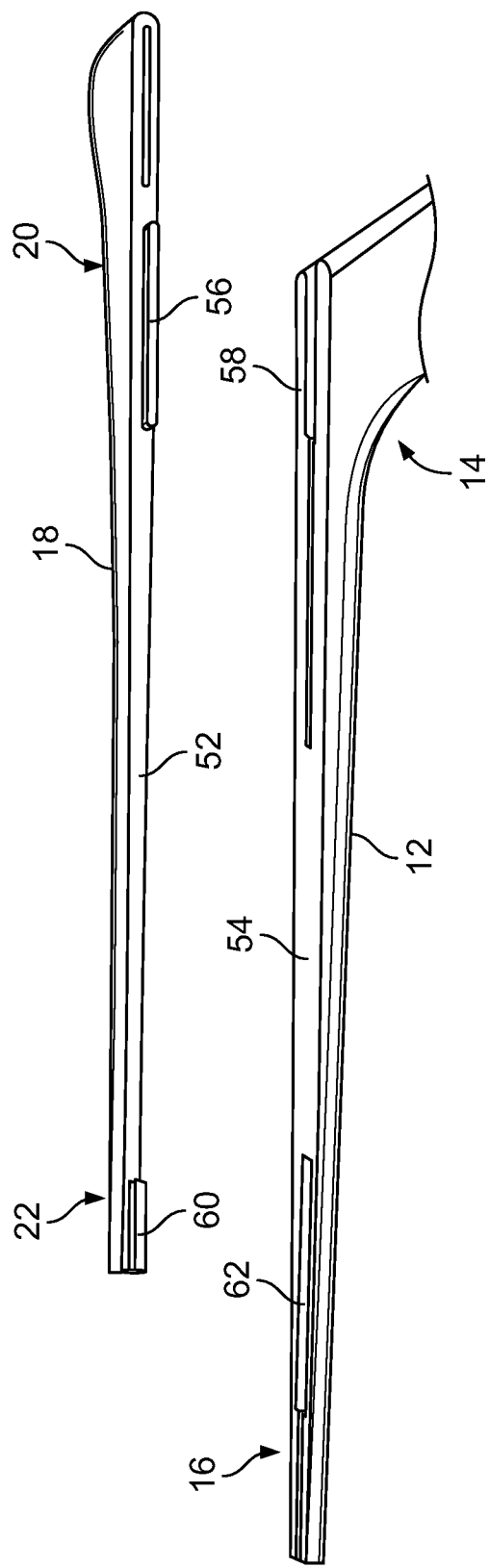
FIG. 2A is a partial exploded, perspective view of the Kerrison rongeur shown in FIG. 1 with the tip assembly removed.
Figure 2B:
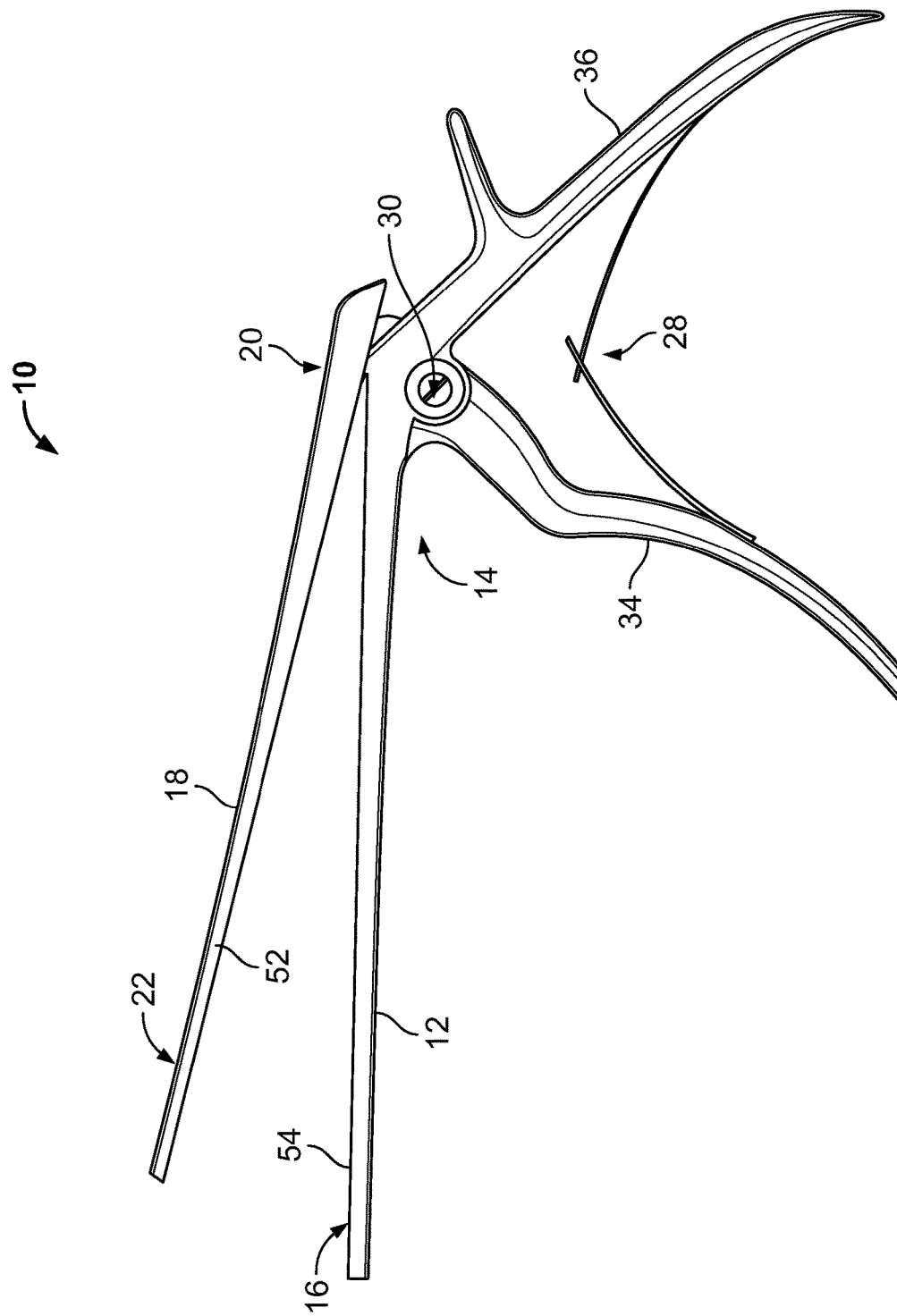
FIG. 2B is a partial exploded, perspective view of an example Kerrison rongeur having a "take-apart" configuration with the tip assembly removed.

FIG. 1 shows an example Kerrison rongeur 10 including a first or stationary arm 12. First arm 12 has a proximal end 14 and an opposing distal end 16. A second or movable arm 18 is slidably coupled to first arm 12. Second arm 18 has a proximal end 20 and an opposing distal end 22. First arm 12 is coupled to second arm 18 such that second arm 18 translates with respect to first arm 12. More specifically, in certain embodiments, proximal end 14 of first arm 12 is coupled to proximal end 20 of second arm 18 and/or distal end 16 of first arm 12 is coupled to distal end 22 of second arm 18. Referring further to FIG. 2A, in particular embodiments, second arm 18 is removably coupled to first arm 12 to facilitate cleaning and sterilizing components of Kerrison rongeur 10 between surgeries or procedures. In alternative example embodiments, such as shown in FIG. 2B, second arm 18 is pivotally coupled to first arm 12 and/or a handle 28. In this configuration, second arm 18 is pivoted or rotated about a pivot point upward relative to first arm 12 without being removed from the device body to facilitate cleaning and sterilizing components of Kerrison rongeur 10 between surgeries or procedures. Kerrison rongeur 10 shown in FIG. 2B may be referred to as having a "take-apart" configuration.

Kerrison rongeur 10 includes a handle 28 operatively coupled to first arm 12 and second arm 18. As used to describe certain embodiments herein, a device body of Kerrison rongeur 10 includes first arm 12, second arm 18 and handle 28. Handle 28 is actuated to urge second arm 18 to move or translate with respect to first arm 12 in opposing directions along a length of first arm 12. For example, in certain embodiments, handle 28 is coupled to first arm 12 at a pivot point 30 using a suitable fastener 32, such as a rivet or bolt. In this embodiment, a first handle portion 34 of handle 28 is moved toward a second handle portion 36 of handle 28 to urge second arm 18 to move along the length of first arm 12 in a distal direction toward a closed position to effectuate cutting during use of Kerrison rongeur 10. A biasing member 38, such as a spring, urges second arm 18 to move in a proximal direction opposite the distal direction toward an open position, as shown in FIG. 1, by biasing first handle portion 34 away from second handle portion 36.

Referring again to FIGS. 1, 2A, and 2B, Kerrison rongeur 10 includes a tip assembly 40 removably coupled to a distal end portion of the device body. In certain embodiments, tip assembly 40 is also disposable. In example embodiments, tip assembly 40 is removably coupled to distal end 16 of first arm 12 and/or distal end 22 of second arm 18. Tip assembly 40 includes a first or bottom tip 42 and a cooperating second or top tip 44 slidably coupled to first tip 42. In example embodiments, a proximal portion or end 46 of first tip 42 is removably coupled to first arm 12 and/or a proximal portion or end 48 of second tip 44 is removably coupled to second arm 18 such that second tip 44 moves with respect to first tip 42 as second arm 18 moves with respect to first arm 12. First tip 42 and/or second tip 44 includes a cutting edge 50 such that as second tip 44 moves with respect to first tip 42 from the open position to the closed position, cutting edge 50 provides an ability to cut biological material including, without limitation, bone, cartilage and/or other fibrous tissue during surgical procedures, for example. Cutting edges 50 may have any suitable shape and/or dimensions, for example, a concave or cupped configuration. Providing a Kerrison rongeur with the ability to change its cutting characteristics greatly increases the flexibility of the Kerrison rongeur over conventional Kerrison rongeurs.

In example embodiments, as shown in FIGS. 2A and 2B, second arm 18 includes a planar surface 52 that contacts a planar surface 54 of first arm 12 when second arm 18 is coupled to first arm 12 to facilitate smooth translational movement of second arm 18 along the length of first arm 12. In certain embodiments, second arm 18 includes a first projection, e.g., a first guide 56, at proximal end 20 that cooperates with a first passage or channel 58 formed in planar surface 54 at proximal end 14 of first arm 12 to couple second arm 18 to first arm 12. Similarly, in certain example embodiments, a second projection, e.g., a second guide 60, at distal end 22 cooperates with a second passage or channel 62 formed in planar surface 54 at distal end 16 of first arm 12. Alternatively, first guide 56 and second guide 60 may be formed on first arm 12 and first passage 58 and second passage 62 may be formed in second arm 18.

In example embodiments, a locking mechanism is configured to removably couple tip assembly 40 to a distal end of the device body of Kerrison rongeur 10. More specifically, first tip 42 is removably coupled to first arm 12 and/or second tip 44 is removably coupled to second arm 18. FIGS. 3-13 show several example embodiments of suitable locking mechanisms for coupling and securing tip assembly 40 to first arm 12 and/or second arm 18. In certain embodiments, first tip 42 is removably coupled to first arm 12 and/or second tip 44 is removably coupled to second arm 18 with tip assembly 40 in an assembled configuration.

Referring further to FIGS. 3 and 4, an example locking mechanism 100 includes a bore 102 formed in distal end 16 of first arm 12. One or more projections 104 extend radially inward from an inner surface 106 at distal end 16 forming bore 102. A first connector 110, such as a pin, is disposed on or extends from proximal end 46 of first tip 42. First connector 110 has an outer surface 112 and a path 114 formed on or in outer surface 112 configured to receive and guide projection 104 with first connector 110 inserted in bore 102. In this embodiment, first tip 42 is rotatable with respect to first arm 12 to move first tip 42 to a locked position. Referring further to FIG. 4, with first tip 42 coupled to first arm 12 and rotated to the locked position, second arm 18 is pivotable with respect to first arm 12, e.g., pivotally movable toward first arm 12, such that a second connector 120, e.g., a T-shaped connector, disposed on or extending from distal end 22 of second arm 18 is positioned or inserted in a corresponding groove 122, e.g., a T-shaped groove, formed in an outer surface 124 of second tip 44. Referring further to FIG. 3, second tip 44 includes a passage or channel 130 formed in a planar surface 132 configured to receive a projection, e.g., a guide 134, formed on a planar surface 136 of first tip 42 that contacts planar surface 132 to slidably couple second tip 44 to first tip 42. Guide 134 positioned within passage 130 provides a stable, movable attachment of second tip 44 to first tip 42. Tip assembly 40 can be removed from the distal end of the device body after use and replaced and disposed of.

Figure 5:
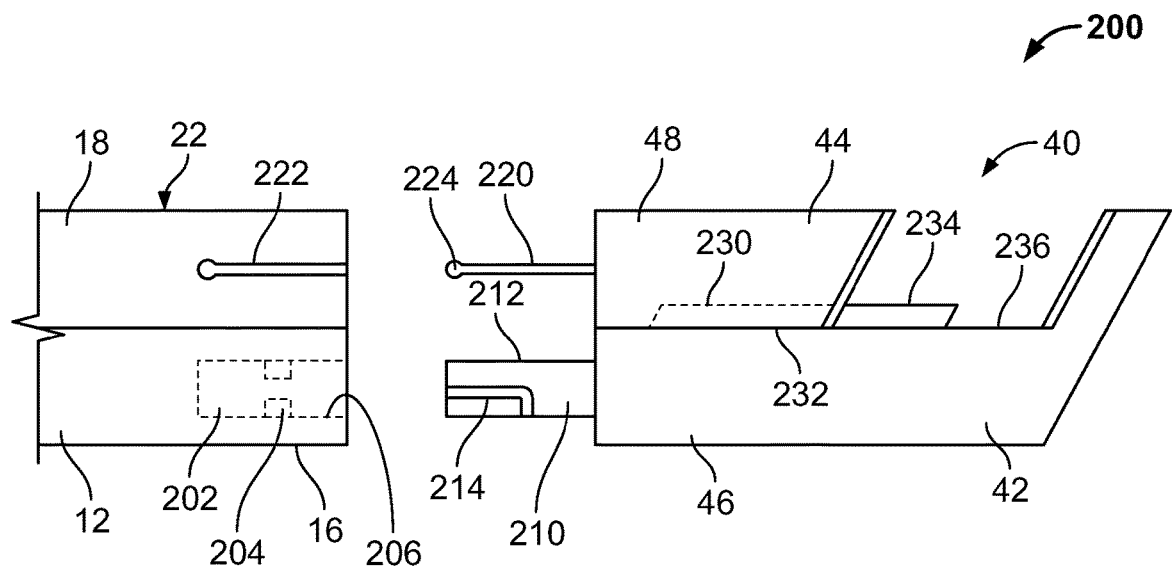
FIG. 5 is a partial side view of an example Kerrison rongeur having a removable tip assembly according to example embodiments.

FIG. 5 shows an example locking mechanism 200 that includes a bore 202 formed in distal end 16 of first arm 12. One or more projections 204 extend radially inward from an inner surface 206 at distal end 16 forming bore 202. A first connector 210, such as a pin, is disposed on or extends from proximal end 46 of first tip 42, and may comprise part of a bayonet connection structure. First connector 210 has an outer surface 212 and a path 214 formed on or in outer surface 212 configured to receive and guide projection 204 with first connector 210 inserted in bore 202. In this embodiment, with first connector 210 inserted in bore 202, tip assembly 40 is rotatable with respect to first arm 12 to move first tip 42 to a locked position. As first tip 42 is rotated to the locked position, a second connector 220, e.g., a pin, extending from proximal end 48 of second tip 44 is moved into a corresponding opening 222, e.g., a slot, formed in distal end 22 of second arm 18 such that second connector 220 is positioned within opening 222. Handle 28 can then be actuated to move second arm 18 distally with respect to first arm 12 and, at the same time, move second tip 44 distally with respect to first tip 42. In certain embodiments, pin 220 includes a ball extension 224 or other suitable extension and opening 222 is sized or configured to accept ball extension 224 to facilitate securing second connector 220 in opening 222. Referring further to FIG. 5, second tip 44 includes a passage or channel 230 formed in a planar surface 232 configured to receive a projection, e.g., a guide 234, formed on a planar surface 236 of first tip 42 that contacts planar surface 232 to slidably couple second tip 44 to first tip 42. Guide 234 positioned within passage 230 provides a stable, movable attachment of second tip 44 to first tip 42. Tip assembly 40 can be removed from the distal end of the device body after use and disposed of.

Figure 6:
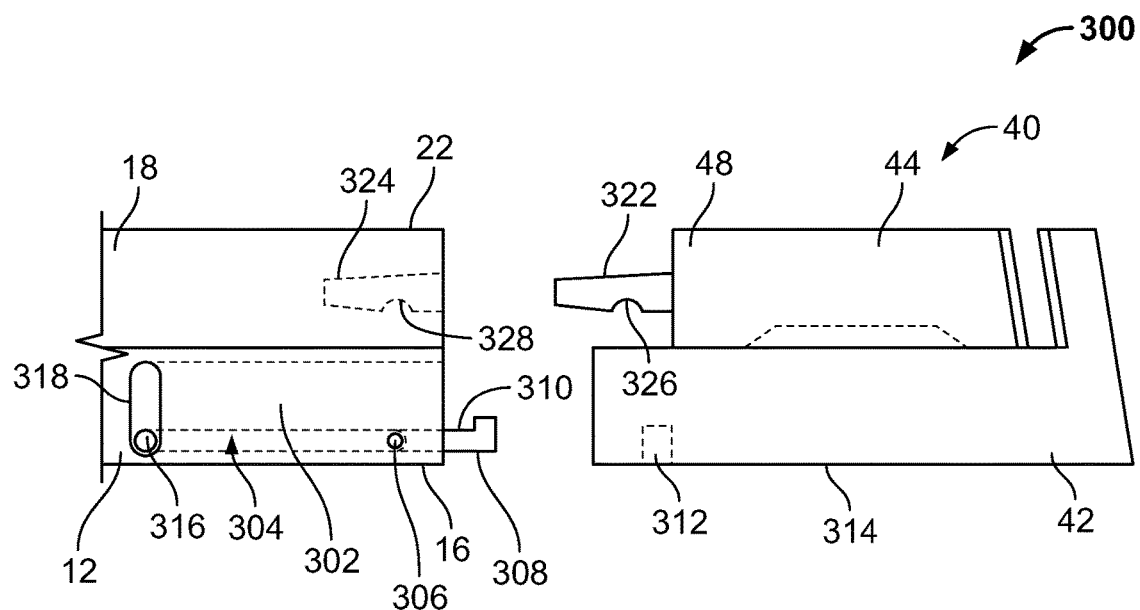
FIG. 6 is a partial side view of an example Kerrison rongeur having a removable tip assembly according to example embodiments.
Figure 7:
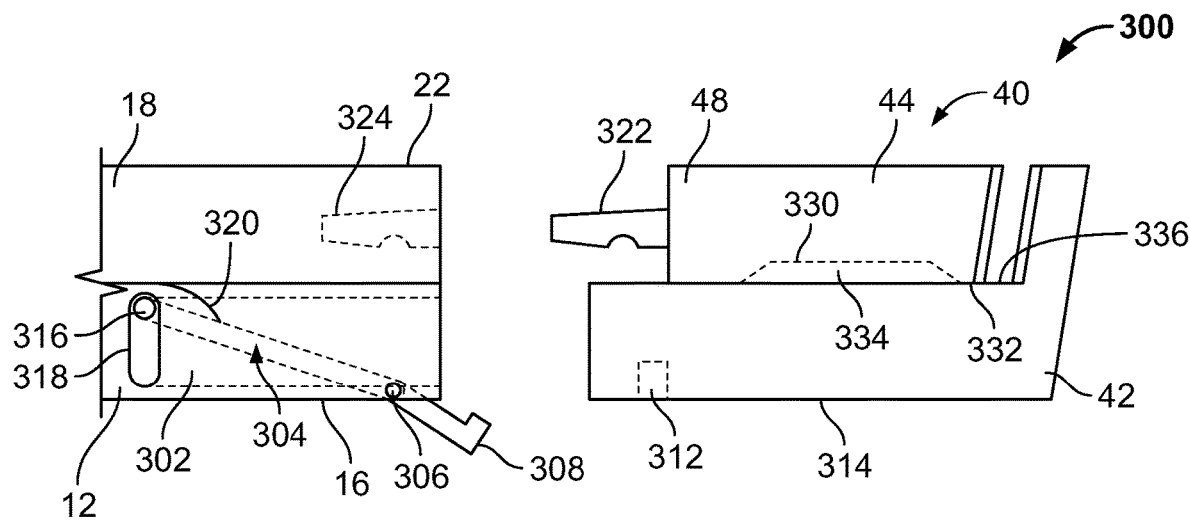
FIG. 7 is a side view of the example Kerrison rongeur of FIG. 6 with the tip assembly being coupled to the distal end of the Kerrison rongeur.

Referring now to FIGS. 6 and 7, in an example alternative embodiment, a locking mechanism 300 includes a bore 302 formed in distal end 16 of first arm 12. A latching element 304 is positioned within bore 302 and pivotally coupled to first arm 12 using a suitable pin 306. A latch 308 is formed on a distal end 310 of latching element 304 that cooperates with a groove or key 312 formed in an outer surface 314 at or near a proximal end of first tip 42 to removably couple first tip 42 to first arm 12. More specifically, latch element 304 is pivoted about pin 306 using a button 316 of latch element 304 which extends through a slot 318 formed some distance proximal of the distal end 16 of first arm 12 to move latch 308 from an initial position to a radially outward position. With latch 308 in the radially outward position as shown in FIG. 7, first tip 42 is moved into contact with first arm 12. Button 316 is released and a biasing member, such as a suitable leaf spring 320, urges latch 308 to move to the initial position to secure latch 308 within groove 312. With first tip 42 coupled to first arm 12, a connector 322, e.g., a pin, extending from proximal end 48 of second tip 44 is inserted into a corresponding bore 324 formed in distal end 22 of second arm 18 and moved to a locked position. In certain embodiments, connector 322 includes one or more depressions 326 that follows a profile of a cooperating projection 328 formed in bore 324 to facilitate securing connector 322 in bore 324. Once connector 322 is positioned in bore 324, handle 28 is actuated to secure second tip 44 to second arm 18. Referring further to FIG. 7, second tip 44 includes a passage or channel 330 formed in a planar surface 332 configured to receive a projection, e.g., a guide 334, formed on a planar surface 336 of first tip 42 that contacts planar surface 332 to slidably couple second tip 44 to first tip 42. Guide 334 positioned within passage 330 provides a stable, movable attachment of second tip 44 to first tip 42. Tip assembly 40 can be removed from the distal end of the device body after use and disposed of.

Figure 8:
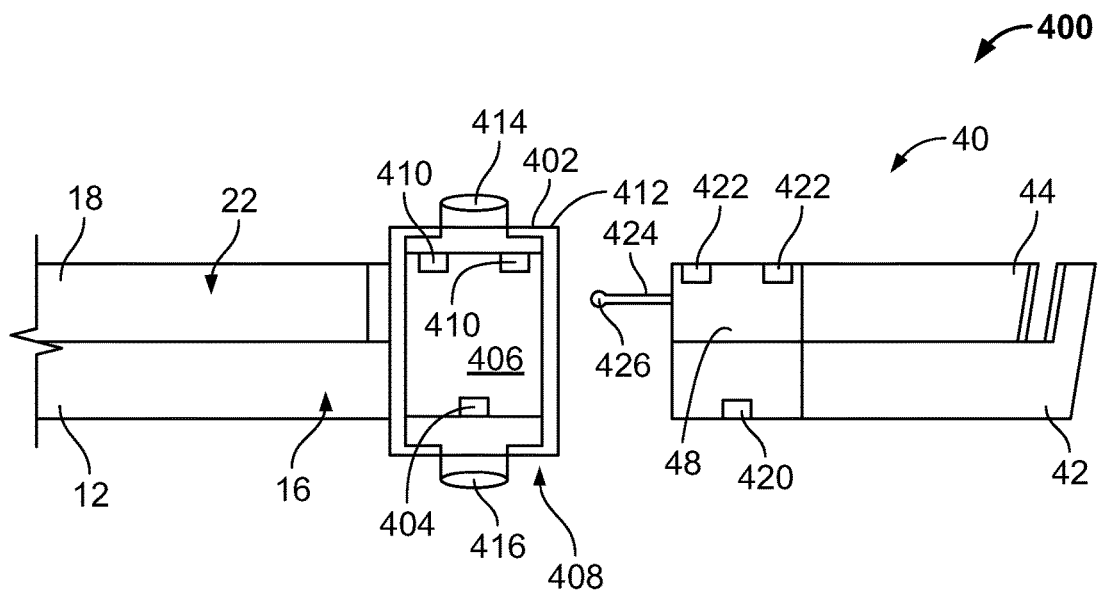
FIG. 8 is a partial side view of an example Kerrison rongeur having a removable tip assembly according to example embodiments.
Figure 9:
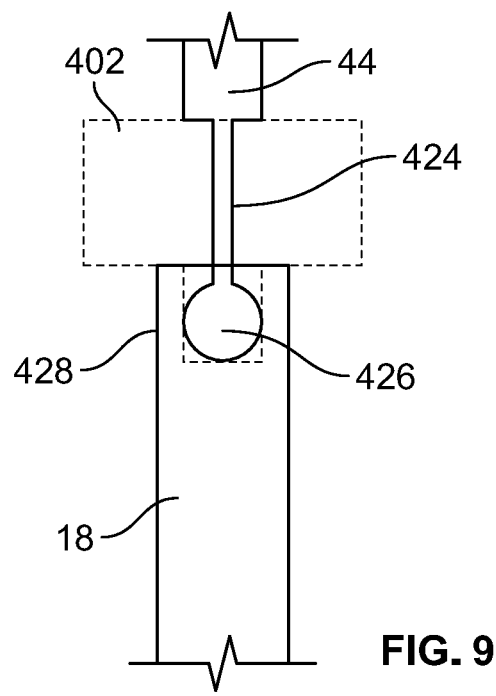
FIG. 9 is a partial top view of the example Kerrison rongeur of FIG. 8.
Figure 10:
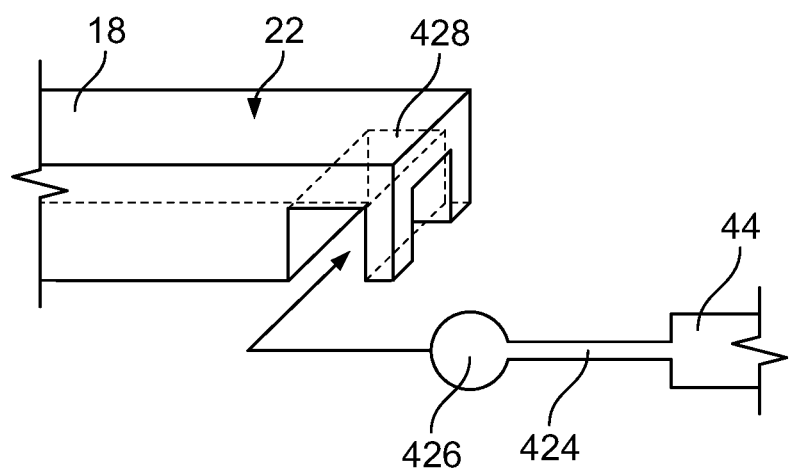
FIG. 10 is a partial exploded, perspective side view of the example Kerrison rongeur of FIG. 8.

FIGS. 8-10 show portions of an example locking mechanism 400 that includes a collar 402 coupled to distal end 16 of first arm 12. Collar 402 includes one or more first projections and/or one or more second projections that are spring-activated to move between a retracted position and an extended position via a corresponding button operatively coupled to the projection or projections. As shown in FIG. 8, a first projection 404 is positioned on a first side 408 of collar 402 to extend into a void 406 of collar 402 in the extended position. Similarly, one or more second projections 410 are positioned on a second side 412 of collar 402 to extend into void 406 of collar 402 in the extended position. In certain embodiments, second projections 410 oppose first projection 404. A first button 414 positioned, in certain embodiments, on second side 412 can be depressed to retract first projection 404 and a second button 416 positioned, in these embodiments, on first side 408 can be depressed to retract second projections 410 to allow tip assembly 40 to be positioned within void 406. Once tip assembly 40 is positioned within void 406, first button 414 is released and corresponding first projection 404 moves from the retracted position to an extended position extending into a cooperating depression 420 formed on or in an outer surface of first tip 42 to couple first tip 42 to first arm 12.

Second button 416 is released and corresponding second projections 410 move from the retracted position to an extended position extending into cooperating depressions 422 formed on or in an outer surface of second tip 44 to couple second tip 44 to second arm 18. In the example embodiment, a connector 424, e.g., a pin, having a ball extension 426 extends from proximal end 48 of second tip 44 and through collar 402 with tip assembly 40 positioned within void 406 such that ball extension 426 extends outside void 406. Referring to FIGS. 9 and 10, second arm 18 includes a receiving section 428 configured to receive ball extension 426 as second arm 18 is pivoted with respect to first arm 12. With ball extension 426 aligned and secured within receiving section 428, second tip 44 is coupled to second arm 18. Once ball extension 426 is positioned in receiving section 428, handle 28 is actuated to lock second tip 44 to second arm 18. Tip assembly 40 can be removed from the distal end of the device body after use and disposed of.

Figure 11:
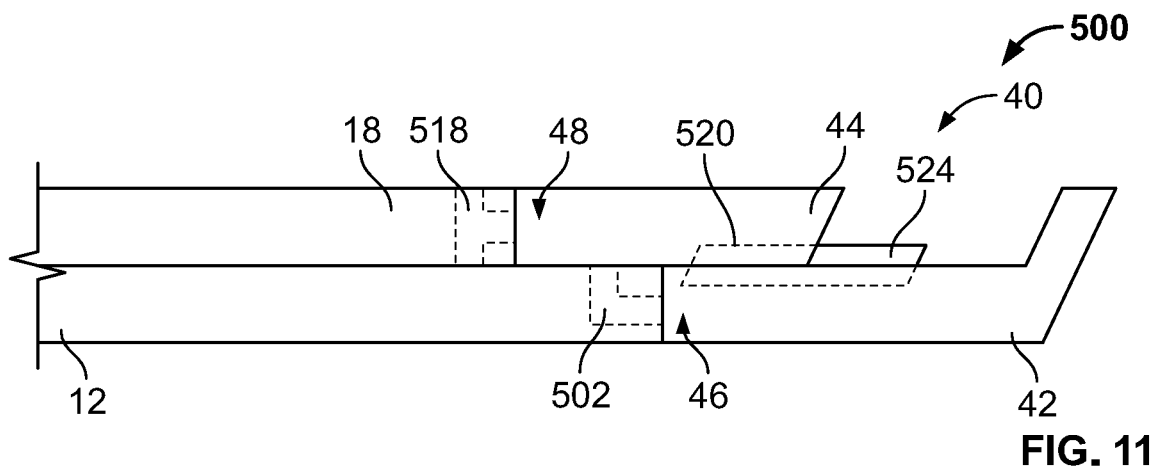
FIG. 11 is a partial side view of an example Kerrison rongeur having a removable tip assembly according to example embodiments.
Figure 12:
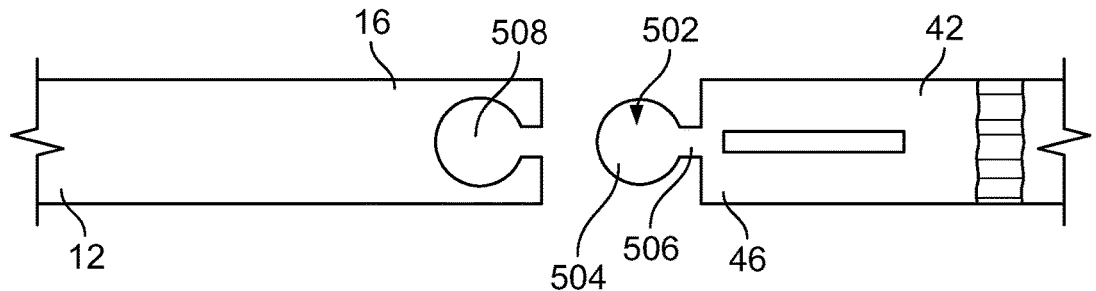
FIG. 12 is a top view of a portion of the removable tip assembly of the example Kerrison rongeur of FIG. 11.
Figure 13:
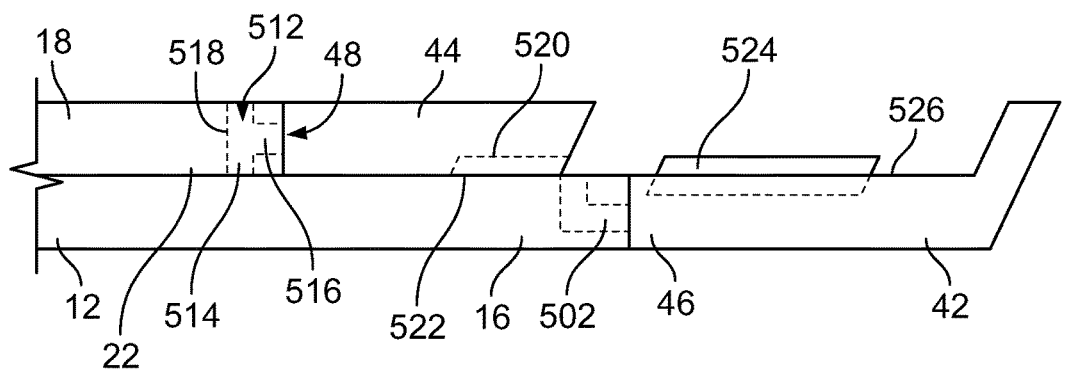
FIG. 13 is a side view of the example Kerrison rongeur of FIG. 11 with the removable tip assembly coupled to a distal end of the Kerrison rongeur.

As shown in FIGS. 11-13, in an example locking mechanism 500, a first attachment member 502 is formed at or near proximal end 46 of first tip 42. In this embodiment, first attachment member 502 includes a tab 504 having a generally circular shape attached to a base portion 506. Tab 504 is slidably positioned within a hole 508 formed in distal end 16 of first arm 12 having a suitable shape configured to accept tab 504 as shown in FIG. 12, for example. With first tip 42 coupled to first arm 12, second tip 44 is slidably coupled to first tip 42 and to second arm 18. More specifically, a second attachment member 512, the same or similar to first attachment member 502 in certain embodiments, is formed at or near proximal end 48 of second tip 44. In this embodiment, second attachment member 512 includes a second tab 514 having a generally circular shape attached to a base portion 516. Second tab 514 is slidably positioned within a hole 518 formed in distal end 22 of second arm 18 having a shape configured to accept tab 514 as shown in FIG. 13, for example. With second tip 44 coupled to second arm 18, handle 28 is actuated to move second tip 44 distally. Second tip 44 includes a passage or channel 520 formed in a planar surface 522 configured to receive a projection, e.g., a guide 524, formed on a planar surface 526 of first tip 42 that contacts planar surface 522 to slidably couple second tip 44 to first tip 42. Guide 524 positioned within passage 520 provides a stable, movable attachment of second tip 44 to first tip 42.

Figure 14:
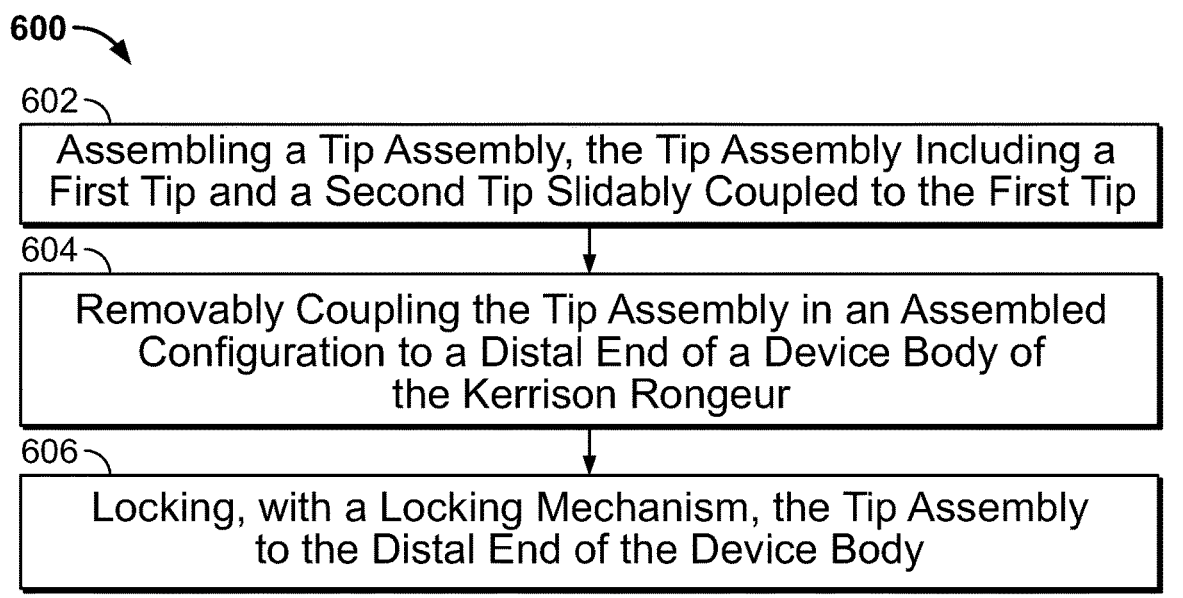
FIG. 14 illustrates steps of an example method for removably coupling a tip assembly to a distal end of a Kerrison rongeur according to example embodiments.

FIG. 14 illustrates steps of an example method for removably coupling a tip assembly to a distal end of a rongeur, e.g., to a distal end of a Kerrison rongeur device body. In example embodiments, a method 600 for coupling a tip assembly to a Kerrison rongeur includes assembling 602 a tip assembly. The tip assembly includes a first tip and a second tip slidably coupled to the first tip. The tip assembly is removably coupled 604 in an assembled configuration to a distal end of a device body of the Kerrison rongeur, such as in the embodiments described herein. The tip assembly is removably secured or locked 606, with a locking mechanism, to the distal end of the device body. After use of the rongeur during a surgical procedure, the tip assembly can be removed, e.g., released, from the device body as an assembled configuration and appropriately disposed of or cleaned and sterilized for further use.

Those of skill in the art will appreciate that embodiments not expressly illustrated herein may be practiced within the scope of the claims, including that features described herein for different embodiments may be combined with each other and/or with currently-known or future-developed technologies while remaining within the scope of the claims. Although specific terms are employed herein, they are used in a generic and descriptive sense only and not for purposes of limitation unless specifically defined by context, usage, or other explicit designation. It is therefore intended that the foregoing detailed description be regarded as illustrative rather than limiting. And, it should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment. In the event of any inconsistent disclosure or definition from the present application conflicting with any document incorporated by reference, the disclosure or definition herein shall be deemed to prevail.

We claim:

1. A Kerrison rongeur comprising:
a stationary arm having a stationary arm proximal end and an opposing stationary arm distal end;
a movable arm slidably coupled to the stationary arm, the movable arm having a movable arm proximal end and an opposing movable arm distal end;
a handle operatively coupled to the stationary arm and the movable arm; and
a tip assembly removably coupled in an assembled configuration to the stationary arm distal end and the movable arm distal end, the tip assembly comprising:
a first tip having a first tip proximal end that abuts the stationary arm distal end at a first interface;
a second tip having a second tip proximal end that abuts the movable arm distal end at a second interface, the second tip slidably coupled to the first tip, the second tip slidably movable with respect to the first tip between an open position and a closed position as the movable arm is slidably movable with respect to the stationary arm;
wherein the first tip or second tip comprises a first connector that extends outward beyond the respective first interface or second interface and into an opening of the respective stationary arm or the movable arm and the other of the first tip or second tip comprises an opening that receives a second connector of the other of the stationary arm or the movable arm that extends outward beyond the other of the first interface or the second interface.

2. The Kerrison rongeur of claim 1, wherein the first connector comprises a projection disposed on the first tip proximal end.

3. The Kerrison rongeur of claim 2, wherein the second connector comprises a projection disposed on the movable arm distal end.

4. The Kerrison rongeur of claim 3, wherein the movable arm rotates relative to the stationary arm thereby moving the projection of the movable arm into the opening of the second tip, the opening of the second tip located through a sidewall of the second tip.

5. The Kerrison rongeur of claim 1, wherein the second tip includes a cutting edge such that as the second tip moves with respect to the first tip from the open position to the closed position, the cutting edge is configured to cut biological material.

6. A rongeur comprising:
a device body comprising:
a first arm having a first arm proximal end and an opposing first arm distal end;
a second arm slidably coupled to the first arm, the second arm having a second arm proximal end and an opposing second arm distal end; and
a handle operatively coupled to the first arm and the second arm, the handle configured to move the second arm along a length of the first arm in a first direction and an opposing second direction; and
a tip assembly removably coupled to the first arm and second arm distal ends of the device body, the tip assembly comprising:
a first tip having a first tip proximal end that abuts the first arm distal end at a first interface;
a second tip having a second tip proximal end that abuts the second arm distal end at a second interface, the second tip slidably coupled to the first tip, the second tip movable with respect to the first tip between an open position and a closed position as the second arm moves in the first direction;
wherein the first tip or second tip comprises a first connector that extends outward beyond the respective first interface or second interface and into an opening of the respective first arm or the second arm and the other of the first tip or second tip comprises an opening that receives a second connector of the other of the first arm or the second arm that extends outward beyond the other of the first interface or the second interface.

7. The rongeur of claim 6, wherein the first connector comprises a projection disposed on the first tip proximal end.

8. The rongeur of claim 7, wherein the second connector comprises a projection disposed on the second arm distal end.

9. The rongeur of claim 8, wherein:
the second arm rotates relative to the first arm thereby moving the projection of the second arm into the opening of the second tip, the opening of the second tip located through a sidewall of the second tip.

10. A method for coupling a tip assembly to a Kerrison rongeur, the method comprising:
assembling a tip assembly, the tip assembly including a first tip and a second tip slidably coupled to the first tip; and
removably coupling the tip assembly in an assembled configuration to a device body of a Kerrison rongeur, the Kerrison rongeur comprising:
a stationary arm having a stationary arm proximal end and an opposing stationary arm distal end;
a movable arm slidably coupled to the stationary arm, the movable arm having a movable arm proximal end and an opposing movable arm distal end;
a handle operatively coupled to the stationary arm and the movable arm; and
the tip assembly removably coupled in the assembled configuration to the stationary arm distal end and the movable arm distal end, the tip assembly comprising:
the first tip having a first tip proximal end that abuts the stationary arm distal end at a first interface; and
the second tip having a second tip proximal end that abuts the movable arm distal end at a second interface, the second tip slidably coupled to the first tip, the second tip slidably movable with respect to the first tip between an open position and a closed position;
as the movable arm is slidably movable with respect to the stationary arm;
wherein the first tip or second tip comprises a first connector that extends outward beyond the respective first interface or second interface and into an opening of the respective stationary arm or the movable arm and the other of the first tip or second tip comprises an opening that receives a second connector of the other of the stationary arm or the movable arm that extends outward beyond the other of the first interface or the second interface.

11. The method of claim 10, wherein the movable arm rotates thereby moving the second connector of the movable arm into the opening of the second tip, wherein the stationary arm includes the opening and the first tip comprises the first connector.

* * * * *